United States Patent
Groeschke et al.

(10) Patent No.: US 9,642,530 B2
(45) Date of Patent: May 9, 2017

(54) APPARATUS AND METHOD FOR MONITORING OF A BODY FUNCTION AND/OR A BODY PROPERTY

(71) Applicant: SANOFI-AVENTIS DEUTSCHLAND GMBH, Frankfurt am Main (DE)

(72) Inventors: Jasmin Groeschke, Frankfurt am Main (DE); Jan-Peter Spengler, Frankfurt am Main (DE); Marc Bender, Frankfurt am Main (DE); Heinz Riederer, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 2 days.

(21) Appl. No.: 14/435,795

(22) PCT Filed: Nov. 1, 2013

(86) PCT No.: PCT/EP2013/072850
§ 371 (c)(1),
(2) Date: Apr. 15, 2015

(87) PCT Pub. No.: WO2014/068077
PCT Pub. Date: May 8, 2014

(65) Prior Publication Data
US 2015/0257646 A1    Sep. 17, 2015

(30) Foreign Application Priority Data
Nov. 5, 2012    (EP) ...................................... 12191186

(51) Int. Cl.
*G08C 19/22* (2006.01)
*G08C 17/00* (2006.01)
(Continued)

(52) U.S. Cl.
CPC .......... *A61B 5/0022* (2013.01); *A61B 5/0002* (2013.01); *A61B 5/024* (2013.01);
(Continued)

(58) Field of Classification Search
CPC .................................................... A61B 5/0402
See application file for complete search history.

(56) References Cited

U.S. PATENT DOCUMENTS

2004/0059205 A1    3/2004  Carlson
2008/0004904 A1*   1/2008  Tran ..................... A61B 5/0006
                                                          705/2
(Continued)

OTHER PUBLICATIONS

European Search Report for EP App. No. 12191186, dated Mar. 19, 2013.
(Continued)

*Primary Examiner* — Joseph Feild
*Assistant Examiner* — Pameshanand Mahase
(74) *Attorney, Agent, or Firm* — McDonnell Boehnen Hulbert & Berghoff LLP

(57) ABSTRACT

The invention relates to an apparatus for monitoring of a body function and/or a body property of a patient having a sensor which determines measurement values with regard to the body function and/or the body property, a unit for detecting a critical condition of the respective body function and/or body property based on the measurement values, a unit for providing alert information to the patient in case a critical condition is detected, preferably optically and/or acoustically, an acknowledgement unit for acknowledging the critical condition and a transmitter for transmitting information with regard to the corresponding body function and/or body property, for example an emergency signal and/or a position information, wherein the transmitter is only activatable in the case, in which after a predefined time
(Continued)

period from the detection of the critical condition the acknowledgement unit has not been operated.

20 Claims, 2 Drawing Sheets

(51) Int. Cl.
    *B60R 25/102*    (2013.01)
    *A61B 5/00*    (2006.01)
    *A61B 5/024*    (2006.01)
    *A61B 5/11*    (2006.01)
    *A61B 5/145*    (2006.01)
    *A61B 5/18*    (2006.01)

(52) U.S. Cl.
    CPC ........... *A61B 5/1112* (2013.01); *A61B 5/1113* (2013.01); *A61B 5/1117* (2013.01); *A61B 5/14532* (2013.01); *A61B 5/18* (2013.01); *A61B 5/746* (2013.01); *A61B 5/747* (2013.01); *A61B 5/749* (2013.01)

(56) References Cited

U.S. PATENT DOCUMENTS

| | | | |
|---|---|---|---|
| 2009/0069642 A1* | 3/2009 | Gao ................... | A61B 5/02055 600/300 |
| 2010/0030092 A1* | 2/2010 | Kristensen ......... | A61B 5/02055 600/509 |
| 2012/0262303 A1* | 10/2012 | Fahey ................. | A61B 5/0006 340/870.02 |
| 2013/0278141 A1* | 10/2013 | Dorf ................. | H01J 37/32183 315/111.41 |

OTHER PUBLICATIONS

International Search Report and Written Opinion for Int. App. No. PCT/EP2013/072850, mailed Dec. 17, 2013.

* cited by examiner

APPARATUS AND METHOD FOR MONITORING OF A BODY FUNCTION AND/OR A BODY PROPERTY

CROSS REFERENCE TO RELATED APPLICATIONS

The present application is a U.S. National Phase Application pursuant to 35 U.S.C. §371 of International Application No. PCT/EP2013/072850 filed Nov. 1, 2013, which claims priority to European Patent Application No. 12191186.1 filed Nov. 5, 2012. The entire disclosure contents of these applications are herewith incorporated by reference into the present application.

TECHNICAL FIELD

The present invention refers to an apparatus for the monitoring of a body function and/or a body property of a patient comprising a sensor which determines measurement values with regard to the body function and/or the body property.

BACKGROUND

Apparatuses for the monitoring of a body function of a patient (human or animal) are known, for example as blood glucose meter or pulse monitor. These devices assess measurement values of a specific body function, such as the concentration of glucose in the blood or the pulse frequency. In most cases those devices are constructed to detect critical conditions, e.g. an elevated pulse frequency, hyperglycemia or hypoglycemia and when necessary give the respective warnings and warning signals.

Further, apparatuses for the monitoring of a body property of a person are known, for example smart phones which determine and store a sequence of geographical positions of a person along his/her covered way using, for example, GPS.

For patients, in particular children or older people, who are undergoing a therapy such as a diabetes treatment, a lapse of the therapeutic target value possess a critical situation, which often cannot be dealt with sufficiently. In this case particularly parents of children, relatives or emergency personnel are interested in being informed about such conditions in order to offer quick and specific help.

The problem of the present invention is to create a device, which monitors the body function and/or body property of a patient and which in case of critical situation initiates practical steps in order to inform relatives or emergency personnel.

SUMMARY

The above-mentioned problem is solved by the apparatus with the features specified in claim 1.

The apparatus according to the invention comprises a sensor for the recording of values of the body function, a unit for detecting a critical, if applicable pathological, condition (hereinafter short: critical condition) of the body function and/or body property based on the measurement values and a unit for providing alert information to the patient in case a critical condition is detected, preferably optically and/or acoustically, an acknowledgement unit for acknowledging the critical condition and a transmitter for transmitting information with regard to the corresponding body function and/or body property, for example an emergency signal and/or a position information, wherein the transmitter is only activatable in the case, in which after a predefined time period after the detection of the critical condition has passed, e.g. several minutes, the acknowledgment unit has not been operated. In case the acknowledgement unit has been operated within the predefined period of time, the unit for transmitting information stays inactive.

Generally a critical condition, respectively the effect of such on the body function, and the measuring values with respect to the body function are defined by the treating health care practitioner (HCP) and/or the respective health authorities. For example it is generally accepted that if the concentration of glucose in the blood falls below a level of 40 mg/dl there is a hypoglycemia and if the concentration exceeds a level of 243 mg/dl (13.5 mmol/l) there is a hyperglycemia. A critical value of the pulse frequency can be determined individually and usually depends on the age and physical condition of the patient.

The apparatus according to the invention has the advantage of not informing the attending person and/or the emergency personnel in every case, which means those cases in which the patient is fine and despite the critical condition able to take the necessary measures herself or himself. Due to this, unnecessary costs and and expenditures are avoided. At the same time, if a patient is actually not doing well because of his or her critical condition or he or she is not able to help himself or herself and does therefore not acknowledge the alert information about the critical condition in the given time, the transmitter is activated and the respective information, e.g. information about the monitored body function and its condition and/or information about the patient or his/her body property is transmitted to the attending person or the emergency personnel, respectively.

Information about the monitored body function and its condition include for example information about what body function is monitored, the current measuring values taken by the sensor and the threshold values on which the detection of a critical condition is based on.

Information about the patient or his/her body property include for example name, address, phone numbers or the current position of the patient, which can be determined for example by an integrated GPS sensor.

Another advantage of the inventive apparatus consists therein that it improves the possibility of older people to stay independently. If a short dysfunction of the body leads to a fall, a height gauge (altimeter) may measure the distance of the gauge fixed at the patient's body with regard to the floor or sensor elements positioned within the flat of the patient. In this case the body property is the position of the height gauge with regard to the floor. This embodiment may only be applied to the "homezone", that means for example the flat of the patient.

In another embodiment the sensor comprises a position sensor like GPS. Further the patient and/or the HCP may define geographical areas and, if applicable, corresponding time information. These areas may be allowed areas and/or forbidden areas. If the position of the patient is detected to be in a forbidden area or outside an allowed area, preferably if the time of the day and/or day of the week is additionally considered, the irregular position is indicated at the display and may be acknowledged by the patient as explained above. That means that allowable areas and/or forbidden areas may be defined dependent on a corresponding time of day and/or day of the week. In case that the patient does not acknowledge the critical condition within the predetermined time period the transmitter is activated and transmits preferably the position of the patient and an emergency signal. This embodiment may be important with regard to dementia or disoriented patients.

In a further embodiment the body property of the patient which is measured by the sensor comprises the time-dependent position change of the sensor. An unusual steadiness in position may have at least two reasons. At first the patient may suffer an illness and therefore does not move. At second the sensor is not worn by the patient. The occurrence of the second case may be distinguished from the first situation by additionally determining the position of the sensor. In case that the sensor is located within a geographical area around the flat of the patient ("homezone"), it is very probable that the sensor is not worn by the patient and lies at home of the patient. Hence, the unit for detecting a critical condition compares the time of steadiness in position with a predetermined time threshold and preferably considers additionally the geographical position of the sensor or the time of day and/or the day of week in order to detect a critical condition in which the patient may need help.

Hence, it is of advantage if the sensor comprises a clock measuring the time and determining the day of week.

The acknowledgement unit may comprise a push-button or a plurality of keys and buttons which have to be pressed simultaneously. Additionally, the acknowledgement unit may comprise a microphone, which receives sound signals from the patient, such as a predefined word or a predefined sentence, then conducts a speech analysis of these sound signals and compares it to the predefined word or sentences. In the latter case acknowledgement can only be made by the patient repeating a predefined word or sentence. By integrating a voice recognition system in the acknowledgement unit which analyzes the sound signals from the patient, it may be ensured that the acknowledgement comes from the respective patient.

In a preferred embodiment of the present invention the transmitter is equipped to transmit a respective emergency call after being activated. The transmitter according to the invention transmits an internationally recognized emergency signal or depending on the country or region, where the patient currently is, a regionally recognized emergency signal to a respective mobile or conventional phone emergency call recipient. This makes it possible for the emergency personnel to be on site very quickly and to help the patient in critical condition.

In a further embodiment of the invention the unit for detection of a critical condition may compare a measurement value of the body function and/or a body property taken by the sensor with at least one threshold value so that the unit can assess, depending on the outcome of this comparison, if there is a critical condition or not. Therein is preferably the at least one individual threshold value to be preset by the patient or the HCP, as this threshold value is subject to fluctuations according to for example the age of the patient. Accordingly, a measurement value recorded by the sensor may be analyzed whether the measurement value lies within an allowed or forbidden measurement range, for example a predefined geographical position or area, and for the measurement value it is then decided whether there is a critical condition or not dependent on the result of the comparison or analysis. The above explanation regarding presetting by the patient or an HCP applies to the allowed or forbidden measurement range analogous.

In another preferred embodiment the transmitter comprises a transmitter for the public mobile phone network, if necessary via satellite. Via the known mobile phone network the information about the patient or the critical condition can be submitted fast and easy and as quickly as possible.

Further, it is of advantage that the transmitter is operable to communicate with a vehicle and/or a mobile phone and/or telephone network, particularly via the conventional telephone network and/or the public mobile phone network. Via those information channels the apparatus according to the invention may, in order to effectively avoid accidents, also transmit information to the vehicle, in which the patient may currently be located. After the transmission of the information of the critical condition of the patient, which may be the driver, the control apparatus of the vehicle may stop the vehicle in a controlled manner and/or show the respective indication and/or request in order to make the driver stop the vehicle.

Additionally, in one embodiment of the present invention there is also the advantage that the fixed time period in which the acknowledgement of the condition by the patient has to be made, may be preset by the patient and/or the HCP.

The above problem is further solved by a method with the features of claim 7.

In particular, the method for monitoring of a body function and/or a body property of a patient comprises the following steps:
  determining measurement values with regard to the body function and/or the body property,
  detecting a critical condition of the respective body function and/or body property based on the measurement values,
  providing an alert information to the patient in case a critical condition is detected, preferably optically and/or acoustically,
  transmitting information with regard to the corresponding body function and/or body property, for example an emergency signal and/or a position information, only in the case, in which after a predefined time period from the detection of the critical condition of this body function and/or body property an acknowledgement of the critical condition has not been detected, wherein the information preferably comprises a stop-instruction for a control apparatus of a vehicle or an indication and/or request for a driver of the vehicle to make the driver stop the vehicle.

As explained above with regard to the apparatus, the inventive method allows that a patient in a really critical situation is effectively helped.

In a preferred embodiment, a determined measurement value is compared with at least one threshold value and/or it is analyzed whether the measurement value lies within an allowed or forbidden measurement range, for example a predefined geographical position or area, and for the measurement value it is then decided whether there is a critical condition or not dependent on the result of the comparison or analysis. Therein, it depends on the type of measurement value whether every measurement value is compared and/or is analyzed or whether the measurement values are compared and/or analyzed in bigger intervals, for example each tenth measurement value is compared and/or analyzed in order to fasten the procedure. The latter possibility is particularly relevant in the case where a critical condition slowly develops and does not abruptly emerge.

In another embodiment for the detection of acknowledgement sound signals are recorded, preferably by a microphone, wherein preferably additionally a speech analysis of the received sound signal and/or a voice recognition of the received sound signal is conducted in order to decide whether the patient acknowledges the critical condition based on the result of the speech analysis of the received sound signal and/or of the voice recognition of the received sound signal.

The invention further refers to a system comprising an above described apparatus for monitoring of a body function and/or a body property of a patient and a control apparatus for a vehicle with a driver, wherein in case the control apparatus receives a stop-instruction or an indication or request to make the driver stop the vehicle from the transmitter of the apparatus for monitoring, which is preferably located within the vehicle, the control apparatus is operable to initiate the stop of the vehicle or to initiate displaying of the corresponding indication or request to the driver of the vehicle and/or to initiate another secure mode of the vehicle like starting the operation of hazard flashes.

Further objectives, characteristics, advantages and applications of the invention may be derived from the following description of the Figures of one embodiment. All described and/or depicted features either individually or in any combination form the subject-matter of the invention, independently from their arrangement in the claims or their back reference.

DETAILED DESCRIPTION

Figure 1:
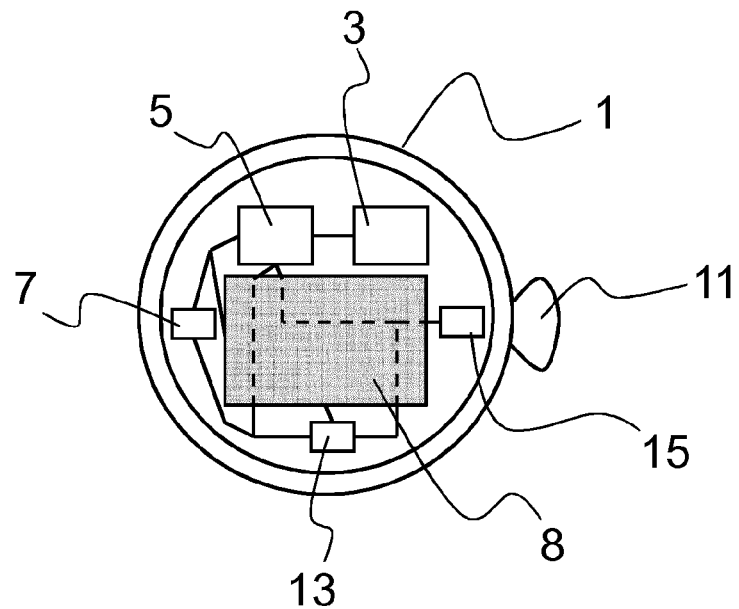
FIG. 1 an apparatus according to the invention shown in a top view in a first situation, FIG. 2 the apparatus according to the invention according to FIG. 1 in an alarm situation and FIG. 3 the apparatus according to the invention according to FIG. 1 in a situation of transmitting information.
Figure 2:
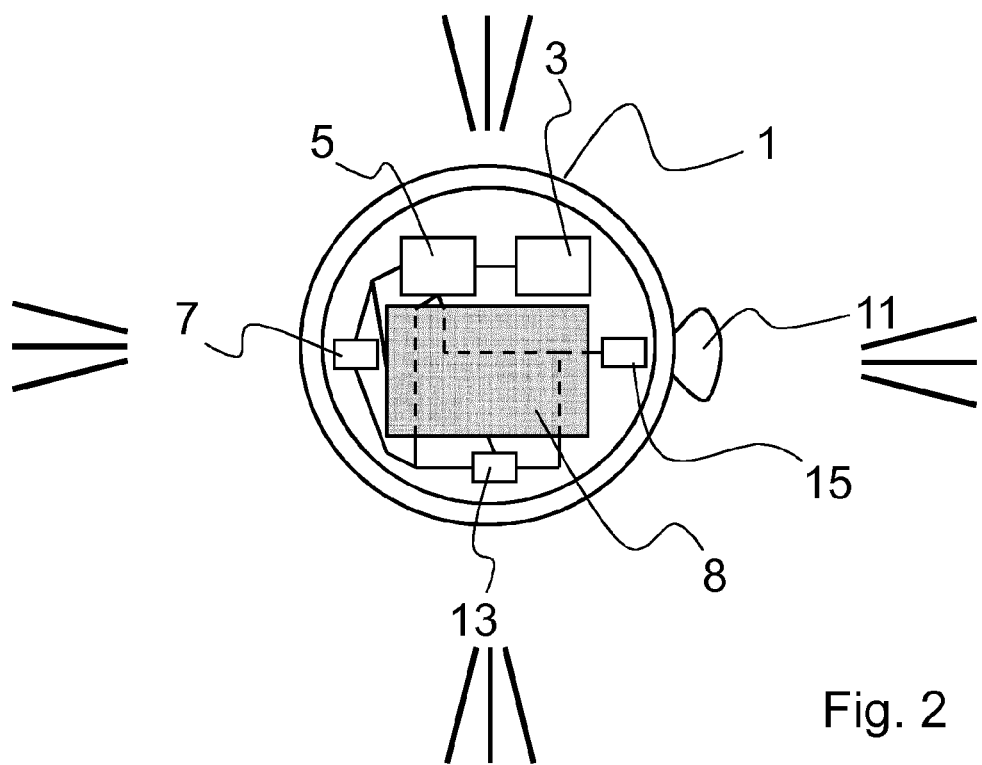
Figure 3:
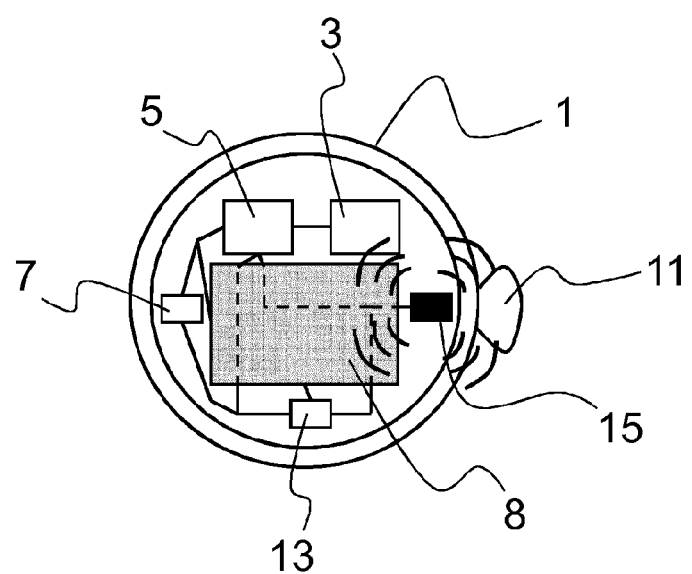

The monitoring apparatus depicted in FIGS. 1 to 3 comprises a housing 1, resembling a watchcase, a sensor for the recording of a measuring value of a body function in form of a pulse frequency sensor 3. Pulse frequency sensors are already known and are therefore in regard to their method of operation not further described.

Furthermore, the housing 1 comprises a device 5 for the detection for a critical condition of the body function. In case of the embodiment described herein, a device 5 is provided, which determines whether the pulse frequency detected by the pulse frequency sensor 3, exceeds a first threshold value of, e.g. 220 $min^{-1}$. Therefore the device 5 is connected with the pulse frequency sensor 3. The threshold value for the pulse frequency saved in the inventive apparatus may be changed by the HCP or the patient.

In case the device 5 detects that the preset threshold value for the pulse frequency is exceeded, the unit for displaying the critical condition generate for example a sharpe tone as an alert information by a loudspeaker 7 and/or a flashing light signal as an alert information by a display 8, informing the patient of the present critical condition. The loudspeaker 7 and/or the display 8 are connected to the device 5. The situation of the inventive apparatus in which a critical condition of the patient has been detected and the loudspeaker 7 generates a sharp warning tone and the display 8 shows a warning signal is depicted in FIG. 2.

Now the patient has the possibility of deciding whether he or she considers this condition to be actually critical and whether he or she is able to take further measures in this case.

If the patient decides that the condition is not so critical that his/her body function is affected or that he or she is able to take the proper countermeasures without help, he or she will acknowledge the warning signal by operating e.g. a push button 11 or alternatively two push buttons at the same time accommodated for example sideways on the housing. The warning signal from the loudspeaker 7 und/or the display 8 will then stop and the inventive apparatus will revert into the normal state as shown in FIG. 1, in which it continuously or in predetermined fixed intervals records a measuring value of a body function or a body property, such as the pulse frequency.

The apparatus according to the invention furthermore comprises a clock 13 with a clock pulse, also arranged within the housing 1, which after the detection of a critical condition of the body function by the device 5 connected with the clock 13, assesses the expiration of a preset time period. Such a time period may be for example 10 minutes. If the warning signal is not acknowledged by the patient as described above within this time period, immediately after expiration of this period, as depicted in FIG. 3, a transmitter 15 is activated, which transmits over a radio network, e.g. a public mobile phone network, information about the physical condition of the patient and/or the patient itself, respectively. The information may be created in such a way that the network provider recognizes the information as a regional or national emergency call. The network provider then transfers this information to an emergency service provider near the patient.

Furthermore the information can also be transmitted to the phone numbers of relatives, such as parents or children, or attending persons, which have before been saved in the apparatus according to the invention.

Now it is possible that the staff of an emergency service respectively the attending persons and relatives can take further measures, in particular offer immediate help for the patient as for example sending an ambulance to the current location of the patient.

Further, the transmitter 15 may comprise a unit for the communication with a vehicle and/or a mobile phone and/or the telephone network. According to the invention, particularly the communication of the apparatus with the vehicle, with which the patient is moving, may be provided as with the emerging of a critical condition there is an increased risk of accidents. If information about the critical situation with regard to a driver is transmitted to the vehicle, it may be possible that the control system/apparatus of the vehicle automatically stops the vehicle or initiates another secure mode of the vehicle like starting the operation of hazard flashes. Therefore, the information transmitted to the vehicle in case a critical condition of a patient is detected comprises a stop-instruction for the control apparatus of the vehicle or an indication and/or request for the driver to make the driver stop the vehicle. Alternatively or additionally, the information may also be transmitted to the patient's own mobile phone from which it may be further transmitted to relatives, attending persons or emergency personnel.

The apparatus according to the invention depicted in FIGS. 1 to 3 may for example be used for monitoring diabetes patients, as the pulse frequency also is an indicator for hyperglycemia or hypoglycemia. In a similar way the apparatus according to the invention may be used for example for monitoring of patients suffering from epilepsy (measuring of absences, measuring via electrodes) or for monitoring of patients suffering from heart conditions (recording of cardiac arrhythmias). In the latter case cardiac arrhythmias may be measured for example by an implanted pacemaker or defibrillator and transmitted the recorded results to the apparatus according to the invention. If necessary the detection of a critical condition may be determined also in the pacemaker or defibrillator. In this case the monitoring apparatus may be connected with the pacemaker or defibrillator. Another example of use refers to older people, in particular patients which suffer dementia or disorientation. The location of these patients may be used to decide whether a critical condition have been occurred, for example in case the patient arrives in a no-go-aera.

The invention claimed is:

1. An apparatus for monitoring of a body function and/or a body property of a patient comprising:
 a sensor which determines measurement values with regard to the body function and/or the body property,
 a detector unit for detecting a critical condition of the respective body function and/or body property based on the measurement values,
 an alert unit for providing alert information to the patient in case a critical condition is detected optically and/or acoustically,
 an acknowledgement unit for acknowledging the critical condition, and
 a transmitter for transmitting, from the apparatus to an emergency service provider, information with regard to the corresponding body function and/or body property,
 a clock for determining a time that has elapsed since a detection of the critical condition by the detector unit,
 wherein the transmitted information includes an emergency signal and/or a position information, and
 wherein the transmitter is only activatable responsive to a determination that both (i) the time determined by the clock to have elapsed since the detection of the critical condition exceeds a predefined time period, and (iii) the acknowledgement unit has not been operated since the detection of the critical condition.

2. The apparatus according to claim 1, wherein the detector unit for detecting a critical condition is operable in such a way that a measurement value recorded by the sensor (i) is compared with at least one threshold value and/or (ii) is analyzed to determine whether the measurement value lies within an allowed measurement range and/or a forbidden measurement range, and
 wherein, for the measurement value, it is then decided whether there is a critical condition or not dependent on the result of the comparison and/or the analysis.

3. The apparatus according to claim 2, wherein the at least one threshold value, the allowed measurement range, and/or the forbidden measurement range is presettable by the patient or a health care practitioner (HCP).

4. The apparatus according to claim 2, wherein the allowed measurement range and/or the forbidden measurement range relates to a predefined geographical position and/or a predefined geographical area.

5. The apparatus according to claim 1, wherein the transmitter comprises a transmitter for a public mobile phone network, a satellite network, and/or a landline telephone network.

6. The apparatus according to claim 1, wherein the transmitter is operable to communicate with a vehicle in which the patient is currently located, and/or a mobile phone.

7. The apparatus according to claim 6, wherein the information transmitted to the vehicle comprises a stop-instruction for a control apparatus of the vehicle or an indication and/or request for the driver to make the driver stop the vehicle.

8. The apparatus according to claim 1, wherein the predefined time period is presettable by the patient and/or a HCP.

9. The apparatus according to claim 1, wherein the acknowledgement unit comprises a push-button and/or a plurality of keys.

10. The apparatus according to claim 1, wherein the acknowledgement unit comprises a microphone and a voice recognition unit configured such that the voice recognition unit analyzes the sound signal received by the microphone to verify that an acknowledgement of the critical condition provided by the acknowledgement unit was provided by the patient.

11. The apparatus according to claim 10, wherein the microphone is configured to receive a sound signal from the patient and the voice recognition unit is configured to conduct speech analysis of the sound signal and compare the analyzed sound signal to one or more predefined words to verify that the acknowledgement was provided by the patient.

12. A system comprising:
 an apparatus for monitoring of a body function and/or a body property of a patient according to claim 1, and
 a control apparatus for a vehicle with a driver, wherein in case the control apparatus receives a stop-instruction or an indication or request to make the driver stop the vehicle from the transmitter of the apparatus for monitoring, which is located within the vehicle,
 wherein the control apparatus is operable to initiate the stop of the vehicle or to initiate displaying of the corresponding indication or request to the driver of the vehicle and/or to initiate another secure mode of the vehicle like starting the operation of hazard flashes.

13. A method for monitoring of a body function and/or a body property of a patient comprising the following steps:
 determining measurement values with regard to the body function and/or the body property,
 detecting a critical condition of the respective body function and/or body property based on the measurement values,
 providing an alert information to the patient in case a critical condition is detected, wherein the alert information is provided optically and/or acoustically,
 determining, using a clock, a time that has elapsed since detecting the critical condition,
 determining that both (i) the time elapsed since the detection of the critical condition exceeds a predefined time period, and (ii) an acknowledgement unit has not been operated to acknowledge the critical condition since the detection of the critical condition,
 transmitting, from the apparatus to an emergency service provider, information with regard to the corresponding body function and/or body property, only responsive to the determination that both (i) the time elapsed since the detection of the critical condition exceeds the predefined time period, and (ii) the acknowledgement unit has not been operated since the detection of the critical condition,
 wherein the information is transmitted as an emergency signal and/or a position information,
 wherein the information comprises a stop-instruction for a control apparatus of a vehicle or an indication and/or request for a driver of the vehicle to make the driver stop the vehicle.

14. The method of claim 13, further comprising:
 comparing a determined measurement value with at least one threshold value and/or analyzing whether the measurement value lies within an allowed measurement range or a forbidden measurement range, and for the measurement value, deciding whether there is a critical condition or not dependent on the result of the comparison and/or the analysis.

15. The method according to claim 14, wherein the patient or a HCP presets the time predefined period, the threshold value, the allowed measurement range, and/or the forbidden measurement range in advance.

16. The method according to claim 14, wherein the allowed measurement range and/or the forbidden measurement range relates to a predefined geographical position and/or a predefined geographical area.

17. The method according to claim 13, wherein the information is transmitted via a public mobile phone network, a satellite network, and/or a landline telephone network.

18. The method according to claim 13, wherein the information is transmitted to a vehicle in which the patient is currently located, and/or to a mobile phone.

19. The method according to claim 13, further comprising:
receiving, using a microphone, a sound signal;
analyzing the received sound signal to verify that an acknowledgement of the critical condition was provided by the patient.

20. The method according to claim 19, wherein analyzing the received sound signal comprises comparing the sound signal to one or more predefined words to verify that the acknowledgement was provided by the patient.

* * * * *